United States Patent
Gunday et al.

(10) Patent No.: US 10,433,821 B2
(45) Date of Patent: Oct. 8, 2019

(54) PRECISION DIRECTED MEDICAL INSTRUMENTS

(71) Applicants: Erhan H. Gunday, Great Neck, NY (US); Lawrence J. Gerrans, San Anselmo, CA (US)

(72) Inventors: Erhan H. Gunday, Great Neck, NY (US); Lawrence J. Gerrans, San Anselmo, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 958 days.

(21) Appl. No.: 13/736,746

(22) Filed: Jan. 8, 2013

(65) Prior Publication Data

US 2014/0194776 A1    Jul. 10, 2014

(51) Int. Cl.
*A61B 10/02*    (2006.01)
*A61B 17/34*    (2006.01)
(Continued)

(52) U.S. Cl.
CPC ...... *A61B 10/0233* (2013.01); *A61B 1/00098* (2013.01); *A61B 17/3478* (2013.01); *A61M 25/0084* (2013.01); *A61B 2017/22071* (2013.01); *A61B 2017/22082* (2013.01); *A61M 25/0155* (2013.01); *A61M 2025/0089* (2013.01); *A61M 2025/0092* (2013.01)

(58) Field of Classification Search
CPC .. A61M 25/01; A61M 25/10; A61M 25/1002; A61M 25/1066; A61M 25/0155; A61M 2025/018; A61M 2025/0086; A61M 2025/009; A61B 10/0233; A61B 1/018; A61B 1/2676; A61B 17/3403; A61B 17/3405; A61B 2010/045
USPC ............ 600/567; 604/96.01, 164.01, 164.03, 604/164.13, 131, 509, 510; 606/192, 194, 606/196, 199
See application file for complete search history.

(56) References Cited

U.S. PATENT DOCUMENTS 4,040,413 A * 8/1977 Ohshiro ............. A61B 1/00082
600/115
6,234,177 B1  5/2001 Barsch
(Continued)

FOREIGN PATENT DOCUMENTS

JP    H05507230 A    10/1993
JP    2002542901 A   12/2002
(Continued)

OTHER PUBLICATIONS

Corresponding English text for WO2012/029535 from Espacenet.*
(Continued)

*Primary Examiner* — David J. McCrosky
(74) *Attorney, Agent, or Firm* — Forge IP, PLLC (57) ABSTRACT

A system for delivering a medical instrument into a bodily cavity is provided, including an outer shaft having an aperture in a side wall thereof, wherein the aperture is provided at a distal portion of the outer shaft, an inner shaft positioned inside the outer shaft and having an inflatable balloon disposed at a distal portion thereof, and a needle member movably disposed in the outer shaft, wherein the needle member extends outwardly from the outer shaft through the aperture when the balloon is inflated.

38 Claims, 8 Drawing Sheets

(51) Int. Cl.
*A61B 1/00* (2006.01)
*A61M 25/00* (2006.01)
A61M 25/01 (2006.01)
A61B 17/22 (2006.01)

(56) References Cited

U.S. PATENT DOCUMENTS

| | | |
|---|---|---|
| 6,283,947 B1 | 9/2001 | Mirzaee |
| 6,564,087 B1 | 5/2003 | Pitris et al. |
| 6,692,466 B1 | 2/2004 | Chow et al. |
| 7,182,756 B2 | 2/2007 | Saeed et al. |
| 7,491,188 B2 * | 2/2009 | Holman et al. .......... 604/103.01 |
| 7,670,282 B2 | 3/2010 | Mathis |
| 7,722,630 B1 | 5/2010 | Stone et al. |
| 7,775,968 B2 | 8/2010 | Mathis |
| 8,177,748 B1 | 5/2012 | Beyerlein |
| 8,226,601 B2 | 7/2012 | Gunday et al. |
| 2002/0072706 A1 | 6/2002 | Hiblar et al. |
| 2002/0161388 A1 * | 10/2002 | Samuels et al. ............. 606/192 |
| 2005/0256410 A1 | 11/2005 | Rabiner et al. |
| 2007/0219451 A1 | 9/2007 | Kula et al. |
| 2008/0065025 A1 | 3/2008 | Jenkins et al. |
| 2008/0154172 A1 | 6/2008 | Mauch |
| 2011/0218494 A1 * | 9/2011 | Gerrans et al. .......... 604/101.05 |
| 2011/0301625 A1 | 12/2011 | Mauch et al. |
| 2012/0053485 A1 | 3/2012 | Bloom |
| 2012/0150210 A1 | 6/2012 | Fan et al. |
| 2012/0226103 A1 | 9/2012 | Gunday et al. |
| 2012/0238816 A1 | 9/2012 | Gunday et al. |
| 2012/0259401 A1 | 10/2012 | Gerrans et al. |
| 2013/0006167 A1 | 1/2013 | Alvarez et al. |
| 2013/0116622 A1 * | 5/2013 | Takagi et al. ................. 604/131 |
| 2013/0178828 A1 * | 7/2013 | Takagi et al. ................. 604/506 |
| 2013/0211379 A1 * | 8/2013 | Clair et al. .................... 604/508 |

FOREIGN PATENT DOCUMENTS

| | | |
|---|---|---|
| JP | 2012157606 A | 8/2012 |
| WO | 9210142 A1 | 6/1992 |
| WO | 0066199 A1 | 11/2000 |
| WO | 2011162100 A1 | 12/2011 |
| WO | WO201229535 A1 * | 3/2012 |
| WO | 2012083155 A2 | 6/2012 |

OTHER PUBLICATIONS

International Search Report & Written Opinion of the International Searching Authority Application No. PCT/US2013/075676 Completed: Feb. 25, 2014; dated Mar. 10, 2014 12 pages.

* cited by examiner

PRECISION DIRECTED MEDICAL INSTRUMENTS

FIELD OF THE INVENTION

The present invention relates to methods and systems for delivering medical devices or instruments to specific cellular locations within and adjacent to bodily tissues and cavities. More specifically, the invention relates to a method and system of delivering a balloon guided medical device or instrument to bodily tissues.

BACKGROUND OF THE INVENTION

In diagnosing and treating diseases of various body cavities and organs, it is necessary to deliver various medical instruments to the organs and tissue sites at specified locations.

In the field of drug delivery, many therapeutic and/or diagnostic agents may not be delivered via traditional drug delivery routes, such as non-invasive peroral, topical, transmucosal or inhalation routes. This is because such therapeutic/diagnostic agents are susceptible to enzymatic degradation or cannot be absorbed into the systemic circulation efficiently due to molecular size and charge issues, and thus, will not be therapeutically effective if delivered via the above mentioned routes.

Often, it is also necessary to deliver medicinal or therapeutic substances to remote and not easily accessible blood vessels and other lumens within body organs, such as lungs. It is also important to be able to deliver defined doses of cytotoxic therapeutic and diagnostic substances directly into target tissue because such substances are often very expensive or are capable of causing serious harm if delivered in excess. Therefore, there is a need for systems and methods capable of delivering therapeutic and diagnostic agents directly to target tissue sites inside a patient's body.

It is also desirable to be able to introduce various medical instruments and devices to targeted tissues to assist in performing drug therapy or related therapeutic or diagnostic procedures, such as biopsy, radio therapy, incisions, laser treatment, etc. Such devices often have to be inserted into and guided through remote and not easily accessible bodily lumens, and then positioned precisely to be able to perform a desired medical procedure.

Several devices have been proposed for a targeted delivery of drugs to internal bodily cavities. For example, U.S. Pat. No. 6,283,947 to Mirzaee discloses a catheter for injecting medication to a specific location within a patient's artery. The catheter includes two drug delivery needles positioned at opposite ends of the catheter shaft and may also include an inflatable balloon positioned between the needles for pushing the needles outwardly upon inflation.

U.S. Pat. No. 6,692,466 to Chow et al. discloses a drug delivery catheter having a balloon disposed at its distal end and a drug delivery assembly, e.g. as needle, disposed in a delivery lumen attached to the balloon wall. During use, the catheter is inserted into a patient's body, the balloon is inflated and the needle is extended out of the delivery lumen on the side of the balloon.

There are also a number of systems designed to introduce various medical devices into bodily lumens. U.S. Pat. No. 7,182,756 to Saeed et al. discloses a device for directing a wire guide including an inflatable balloon or an expandable wire basket positioned at a distal end of a catheter shaft, and a guide wire extended out of an opening in the shaft proximal of the balloon. When the balloon or basket is expanded, it comes into contact with the guide wire and is capable of deflecting it.

U.S. patent application No. 2012/0053485 to Bloom discloses a catheter having a biopsy needle and one or more expandable support members coupled to the outer surface of a catheter shaft for anchoring the catheter within a bodily cavity. The needle and the catheter shaft with the balloon may be positioned side by side inside an outer sheath and extended out of the outer sheath once inserted into a patient's body. The needle extends at a non-zero degree angle which may be varied by expansion of the balloon.

While the above described systems are useful for delivering the drugs and related medical instruments/devices to a specific location within a patient's body, these systems still suffer from a number of disadvantages and drawbacks. One of the major problems with the prior art systems described above is that is that they are rather bulky and complex in structure, which makes them unsuitable for use in bodily cavities having a very small diameter, such as lungs. Additionally, these known systems are typically constructed with expensive materials and require multiple working components, and therefore have to be reused multiple times, which requires complex sterilization procedures.

Another problem is that the structure of the devices described above does not allow for optimally safe insertion and operation of the devices in a patient's body. In particular, in the devices discussed above, sharp portions of drug delivery needles or other medical devices are either exposed to surrounding tissue during the insertion or retraction of the device, or become abruptly exposed to surrounding tissue once a protective sheath is removed. This increases chances of harmful injury to surrounding bodily cavities and tissues during operation of the devices. Furthermore, the known devices do not provide a safety mechanism to prevent the drug delivery needles or other sharp instruments from accidentally puncturing the inflatable balloon during the procedure.

A further deficiency of the prior art systems described above is that they are not capable of being positioned as optimally and precisely as may be desired. The known devices do not provide illumination and a direct visual feedback of the area ahead, behind, and around the device to optimize positioning and operation of the device.

Yet another shortcoming of the known systems is that they lack the capability to precisely gauge the size of the environment in which they are being used to provide physiological measurements and feedback that could aid precise and secure positioning and operation of the device. For example, the prior art devices do not enable the surgeon to measure the intra-lumen dimensions of the bodily cavity in which the device is to be operated, and provide no way to accurately adjust for changes in these dimensions during the procedure. Furthermore, the known devices are not capable of accounting for one or more vital signs and physiological parameters of the patient facilitate more precise positioning of the desired medical device/instrument relative to target tissue site.

What is desired, therefore, is an improved system and method for delivering various medical instruments and devices to specific locations inside a patient's body that address the disadvantages and shortcoming of the prior art systems described above.

SUMMARY OF THE INVENTION

In order to achieve at least the above-mentioned objects of the present invention, a system for delivering a medical instrument into a bodily cavity is provided, including an outer shaft having an aperture in a side wall thereof, wherein the aperture is provided at a distal portion of the outer shaft, an inner shaft positioned inside the outer shaft and having an inflatable balloon disposed at a distal portion thereof, and a needle member movably disposed in the outer shaft, wherein the needle member extends outwardly from the outer shaft through the aperture when the balloon is inflated. The system of the present invention can be made in a variety of sizes and have an outer diameter appropriate such that it can be deployed through a working channel of standard bronchoscopes.

In some embodiments, the needle member extends outwardly from the outer shaft at an angle relative to a longitudinal axis of the outer shaft when in an activated position. In certain of these embodiments, the angle at which the needle member extends from the outer shaft is in the range of from about ten (10) degrees to about sixty (60) degrees.

In some cases, a distal end of the needle member extends past the aperture in the distal direction of the outer shaft when in an inactivated position.

In certain embodiments, the system further includes a stop member provided on the needle member to prevent advancement of the needle member past the balloon in a proximal direction of the outer shaft.

In some embodiments, the system also includes an actuation member provided at a proximal end of the outer shaft for moving the needle member between an activated position and an inactivated position. In certain of these embodiments, the actuation member enables rotational movement of a distal end of the needle member.

In some embodiments, the system further includes a fluid source that supplies fluid to the balloon via a lumen of the inner shaft to inflate the balloon. In certain of these embodiments, the fluid source is an electro-pneumatic pump. In additional of these embodiments, the fluid is a gas.

In some cases, the balloon has a wall with a textured outer surface. In certain cases, the textured surface of the balloon comprises a mesh disposed on the balloon wall. In some of these cases, the mesh comprises elastane.

In some embodiments, the system includes at least one imaging marker positioned at the distal end of the outer shaft adjacent the aperture.

In certain embodiments, the outer shaft includes an expansion apparatus affixed to the side wall of the outer shaft opposite the aperture.

In some embodiments, the needle member has a lumen fluidly connected to an opening at a distal end of the needle member. In certain of these embodiments, the needle member delivers a therapeutic and/or diagnostic agent to tissue via the opening at the distal end. In additional of these embodiments, the needle member obtains a tissue sample via the opening at the distal end. In further of these embodiments, the lumen of the needle member accommodates a medical instrument.

In some cases, the needle member has a first lumen fluidly connected to a first opening at the distal end of the needle member and a second lumen fluidly connected to a second opening at the distal end of the needle member.

In certain embodiments, the needle member comprises a memory-shape material.

In some cases, the system also includes an imaging device disposed in the outer shaft for viewing tissue in the bodily cavity. In certain of these embodiments, a distal end of the imaging device extends out through the aperture for viewing surrounding tissue. In other embodiments, the imaging device is disposed in the inner shaft and extends our through an opening inside the inflatable balloon, and an outer wall of the balloon is transparent for viewing surrounding tissue via the imaging device.

In certain embodiments, the system further includes a second inner shaft positioned inside the outer shaft and having a second inflatable balloon disposed at the distal end thereof.

In some embodiments, the outer shaft includes a first lumen for containing the inner shaft and a second lumen for containing the needle member.

A system for delivering a medical instrument into a bodily cavity is also provided, including an outer shaft having an aperture in a side wall thereof, wherein the aperture is provided at a distal portion of the outer shaft, an inner shaft positioned inside the outer shaft and having an inflatable balloon disposed at a distal portion thereof, and a medical instrument movably disposed in the outer shaft, wherein the medical instrument extends outwardly from the outer shaft through said aperture when the balloon is inflated.

In some embodiments, the medical instrument is a biopsy instrument. In additional embodiments, the medical instrument is a drug delivery device. In further embodiments, the medical instrument is a diagnostic device. In yet further embodiments, the medical instrument is an energy emitting source.

A method for delivering a medical instrument into a bodily cavity is further provided, including the steps of inserting an outer shaft into a bodily cavity, the outer shaft having an inner shaft and a needle member disposed therein, and further having an aperture in a side wall thereof at a distal portion of the outer shaft, and inflating a balloon disposed at a distal portion of the inner shaft by supplying fluid thereto such that the balloon contacts the needle member and causes it to extend outwardly from the outer shaft through the aperture.

In some embodiments, the method further includes the step of extending the needle member past the aperture in the distal direction of the outer shaft before inserting the outer shaft into the bodily cavity.

In certain embodiments, the method also includes the step of retracting the needle member in a proximal direction of the outer shaft after the shaft is inserted until the needle member is positioned adjacent the aperture. In some of these embodiments, a stop member is provided on the needle member to prevent advancement of the needle member past the balloon in the proximal direction of the outer shaft.

In some cases, the needle member extends outwardly from the outer shaft at an angle relative to a longitudinal axis of the outer shaft when the balloon is inflated.

In certain embodiments, the method also includes the step of puncturing balloon wall via the needle member.

Other objects of the invention and its particular features and advantages will become more apparent from consideration of the following drawings and accompanying detailed description.

DETAILED DESCRIPTION OF THE INVENTION

Figure 1:
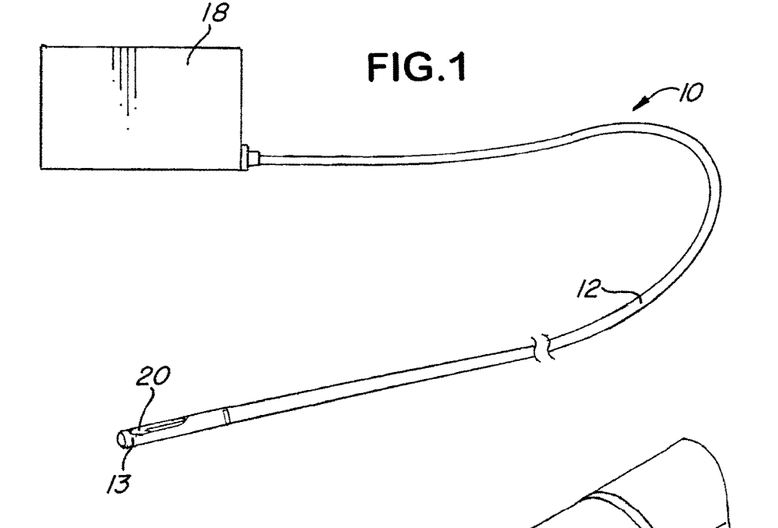
FIG. 1 is a schematic view of a system for delivering a balloon guided medical instrument in accordance with the invention.

The basic components of one embodiment of a system for delivering a balloon guided medical instrument in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system for delivering a balloon guided medical instrument of the present invention may be used to perform various diagnostic and/or therapeutic procedures in specific locations within a patient's body. For example, the present invention can be used to deliver drugs, radiation therapies, chemo therapies, pharmacologic medicines, therapeutic agents, immuno-therapies, biologic materials, biologic markers, radiopaque contrasts, diagnostic agents and related technologies to specific cellular locations within and adjacent to bodily cavities, such as tubular structures, lumens, pleural cavities, airways, vessels, organs, bones and joints. The system of the present invention can also be used to deliver a variety of medical instruments, such as imaging devices, catheter devices, laser fibers, electrocautery probes, diagnostic devices, energy emitting devices, surgical instruments and tools, operative devices, implants and related medical diagnostic and treatment systems. The system of the present invention can be made in a variety of sizes and have an outer diameter appropriate such that it can be deployed through a working channel of standard bronchoscopes.

The system for delivering a balloon guided medical instrument can be introduced into a patient's bodily cavity independently, or may be deployed via, for example, a guiding catheter, a working channel of a rigid or flexible endoscope, or any other suitable guiding device. In one advantageous embodiment, the system is used with a steerable catheter system described in U.S. patent application Ser. No. 13/037,874, the disclosure of which is also incorporated by reference herein in its entirety.

FIG. 1 illustrates one exemplary embodiment of the system for delivering a balloon guided medical instrument in accordance with the present invention. The system (10) includes an outer shaft (12) that houses various components of the system. The outer shaft (12) may have any suitable diameter and length depending on a particular application and/or dimensions of target bodily cavity, and may be flexible, rigid or semi rigid.

The outer shaft (12) may be made with any commercially available material that is flexible enough to allow the shaft to be safely inserted through the available opening of a bodily cavity such that it will deflect from the walls of the cavity instead of puncturing them. In particular, a distal end section (13) of the outer shaft (12) is made flexible to ensure safe and atraumatic insertion of the shaft into bodily cavities.

In some embodiments, the outer shaft (12) may include a coating made of suitably smooth material to facilitate the movement of the shaft through the bodily cavities. In some advantageous embodiments, the outer shaft (12) may consist of a coil wire made of any suitable material, such as stainless steel, and a coating made of suitable materials, such as polyethylene, polyurethane, Pebax® and the like. A braided sheath may also be used instead of the coil wire. In some advantageous embodiments, the coil wire or the braided sheath may be made with a memory shape material, such as nitinol.

In further advantageous embodiments, the outer shaft (12) may include a combination of braided sheath and coil wire materials to provide for optimal flexibility and maneuverability of the shaft. For example, the distal portion (13) of the outer shaft (12) may be made with coiled wire material and the rest of the shaft may be made with the braided sheath material.

The coil wire or braid can be molded over during the shaft extrusion process and can run the entire length of the outer shaft (12). Alternatively, the outer shaft (12) may be molded or extruded in a first step and the coil wire may be disposed within an inner lumen of the outer shaft. Such design improves torque, maneuverability, and kick resistance of the outer shaft (12), and also prevents reduction of the shaft's inner diameter.

Figure 2A:
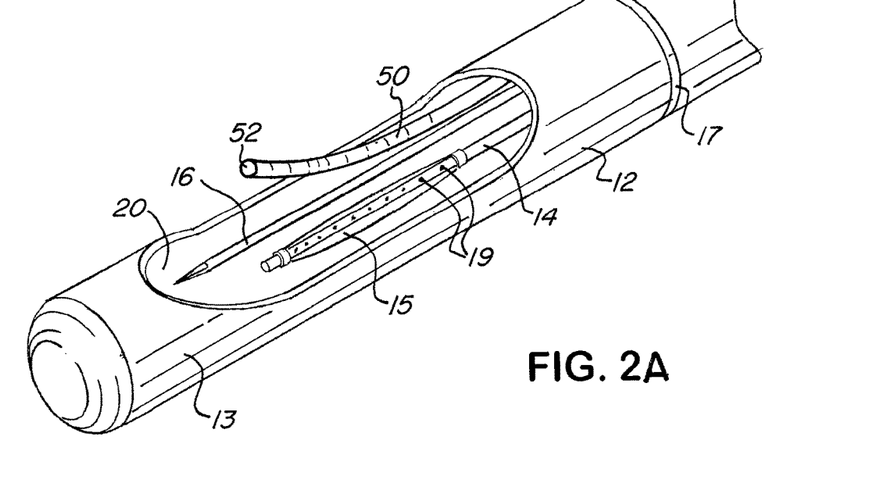
FIG. 2A is an enlarged perspective view of a distal portion of the system of FIG. 1.

In some advantageous embodiments, such as shown in FIG. 2A, the outer shaft (12) may further include imaging markers (17) positioned at the distal end (13) of the shaft or at any other location along the shaft to facilitate external imaging thereof, and to thereby allow for better visualization during insertion and positioning of the system (10) in bodily cavities.

The system (10) further includes an inner shaft (14) positioned inside the outer shaft (12), as illustrated in more detail in FIG. 2A. Similar to the outer shaft, the inner shaft may be made with any suitable material, such as described above, and may have any suitable diameter and length depending on a particular application and/or dimensions of target bodily cavity. An outer diameter of the inner shaft (14) is less than an inner diameter of the outer shaft (12) such that the inner shaft (14) fits inside the outer shaft (12) and is easily movable therein.

The inner shaft (14) has an inflatable balloon (15) positioned at or near the tip of the distal end. The inflatable balloon (15) may be made of latex, Yulex, polyurethane, silicon, chronoprene, chronoflex, chronosil, nylon or other suitable material, and may come in a variety of sizes and diameters, depending on a particular application. In certain advantageous embodiments, a compliant balloon is employed. In further advantageous embodiments, the inflatable balloon (15) may comprise a plurality of balloons/bladders, which may be controlled, inflated and deflated independently of each other.

Figures 3A, 3B, 3C:
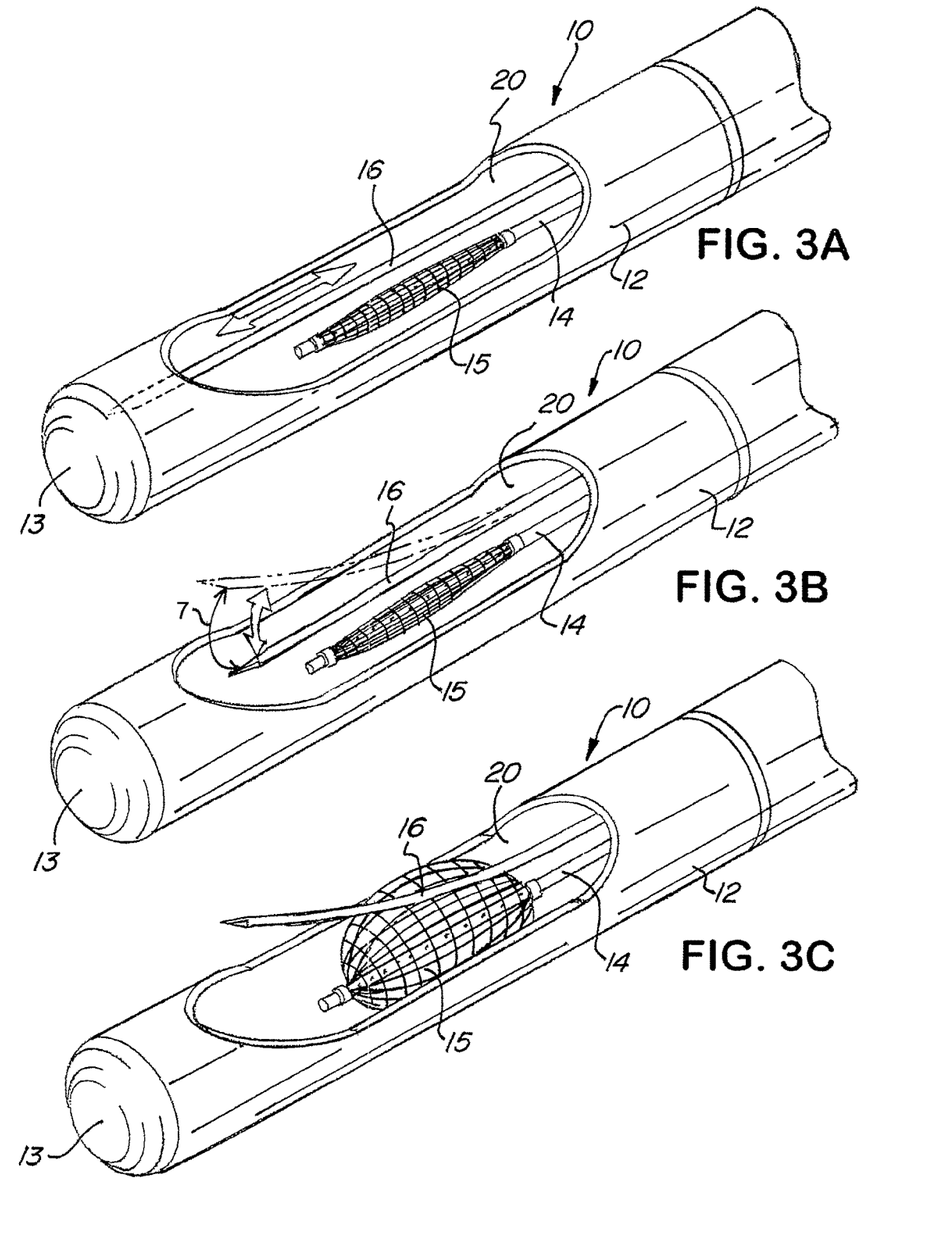
FIGS. 3A-3C are enlarged perspective views of the distal end of the system of FIG. 1, showing operation of various components of the system.

The inflatable balloon (15) may also have an outer wall with a textured surface, such as a woven mesh, as shown in FIG. 3C. The textured surface assists in precisely guiding and positioning the medical instrument by ensuring that it does not slip off the balloon outer surface, and also ensures more uniform expansion of the balloon (15) upon inflation. The textures surface may be made by a woven mesh disposed on the outer surface of the balloon. The mesh may be made of elastane, latex, polyurethane, composite springs, metallic fibers, elastic, steel fibers, or other appropriate material, or a composite or coating thereof. A mesh sleeve may be disposed on the outer surface of the balloon (15) by using any suitable manufacturing method. Alternatively, a mesh sleeve may be knitted or woven from thread directly onto the balloon (15). In other advantageous embodiments, dimensional surface structures, such as bumps or inflatable sinuses, that are encapsulated in the surface substrate of the balloon (15) may be used to produce the surface protrusions forming the textured surface.

In certain advantageous embodiments, the balloon (15) includes imaging markers, such as radio opaque rings, located at or near the ends thereof. Such markers can be selected and appropriately positioned in order to reflect or block the relevant waves of various imaging modalities (e.g., x-ray) in order to allow the use of such modalities to assist with the precise positioning of the balloon (15) and a medical instrument guided by the balloon within a bodily cavity. Similarly, the balloon or balloon mesh may include a radiopaque material, such as a mesh made of yarn having radiopaque iron fibers.

The inner shaft (14) has at least one inner lumen for supplying fluid to the balloon (15) to inflate it. As shown in FIG. 1, the inflation lumen is connected to a fluid source (18), such as a syringe or a pump, connected to a proximal end of the outer shaft (12) via a suitable connection mechanism. The inflation lumen of the inner shaft (12) is in fluid communication with the interior of the inflatable balloon (15) via a plurality of openings (19) in the shaft wall positioned inside the balloon (15), as illustrated in FIG. 2A. Any suitable fluid source may be used in accordance with the present invention.

In one advantageous embodiment, the fluid source (18) is an electro-pneumatic pump having controls on the front thereof, from which a physician or assistant can control the system (as well as a remote control unit), such as that disclosed in U.S. Pat. No. 8,226,601 to Gunday et al., the disclosure of which is hereby incorporated by reference herein in its entirety. The pump (18) supplies a fluid, such as a gas, liquid, or mixture thereof, to the inner shaft (14) via an inflation port to inflate the balloon (15). In certain advantageous embodiments the pump (18) also supplies a therapeutic and/or diagnostic agent, a drug, gel, nanoparticle or mixture thereof, to the inner shaft (14) via the inflation port. The pump (18) also includes a variety of capabilities for balloon identification, proper inflation/deflation of the balloon, and feedback measurements, many details of which are described in Gunday et al. In certain advantageous embodiments, the pump (18) further includes a vacuum source to evacuate fluid from the balloon (15). In other embodiments, a handheld pump or a syringe is used as a fluid source.

In some embodiments, the system (10) includes a data device, such as optical. RFID, flash memory, etc. This way, the pump (18) is able to identify the type of system that is connected to it and read the characterization data of the balloon, e.g. maxim pressure, volume, dimensions, etc., and then adjust its control accordingly based on user input.

The pump (18) may further include a processor to control the supply of fluid to the inflatable balloon (15) based on at least one predetermined parameter. In some embodiments, such predetermined parameters may be manually entered by the user. Alternatively, the control of the fluid is based on default parameters selected by the pump (18), which are based on the characteristics of the particular balloon and/or measurements of dimensions of a particular bodily cavity made by the pump. Furthermore, the pump may control and regulate the pressure by monitoring and taking into account one or more vital signs and physiological parameters of the patient, such as body temperature, heart rate, blood pressure, and respiratory rate.

Figures 10, 11:
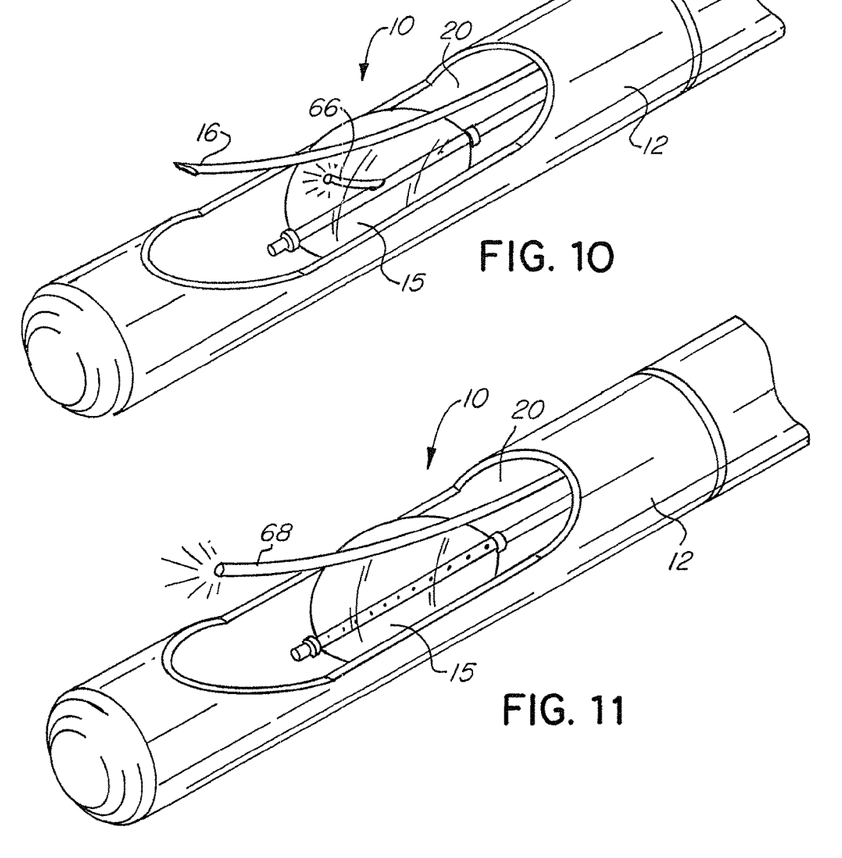
FIG. 10 is an enlarged perspective view of the distal end of the system of FIG. 1, showing an imaging device positioned inside the balloon.
FIG. 11 is an enlarged perspective view of the distal end of the system of FIG. 1, showing an energy delivery device.

It should be noted that the inner shaft (14) may have additional lumens for various purposes, for example, for introduction of an imaging device and/or an illumination device to assist in proper positioning of the balloon together with a desired medical device relative to a target tissue site. In one advantageous embodiment, an outer wall of the inflatable balloon (15) is transparent, and an imaging device, an illumination device, and/or energy source disposed in the inner shaft (14) extends out through one of the openings (19) inside the balloon for viewing and/or delivering energy to the surrounding tissue. For example, as shown in FIG. 10, an imaging device (66) extends out through one of the openings inside the balloon. In another advantageous embodiment, the distal end of the inner shaft (14) includes a transparent membrane, such that the imaging/illumination device or energy source positioned in the inner shaft lumen is capable of viewing/modifying the tissue in front of the balloon (15) through the transparent membrane. In yet another advantageous embodiment, the distal end of the inner shaft (14) has an opening, and the imaging and/or illumination device or energy source is extended out of the inner shaft through the opening for viewing and/or modifying the surrounding tissue. A distal tip of the imaging/illumination device and/or energy source may be rotatable such that a complete 360 degree view of the surrounding tissue may be obtained.

The outer shaft (12) has an aperture (20) in a side wall thereof, as shown in FIG. 2A. The aperture (20) is provided at a distal portion of the outer shaft (12) and adjacent the distal end (13) thereof. The aperture (20) may have any suitable configuration and dimensions depending of a type of the balloon used and a particular medical device/instrument being delivered. Preferably, the aperture is large enough to accommodate the balloon (15) in its fully inflated state such that the balloon extends partially out from the outer shaft wall when fully inflated, as illustrated in FIG. 3C.

As shown in FIG. 2A, the aperture (20) opening extends less than one half of circumference of the outer shaft (12). It is noted, however, that in some embodiments, the aperture opening may extend substantially more or substantially less than one half of the circumference depending on a particular application and a type of device being delivered. There is a space provided between a distal end of the aperture (20) and the distal tip (13) of the outer shaft (14) that is completely enclosed by the outer shaft wall for housing the medical instrument or device during the insertion of the system into a patient's body, as illustrated in FIG. 3A and discussed more fully below.

The system (10) of the present invention can be used for delivering any type of a medical instrument or device into a bodily cavity. In the embodiment shown in the figures, a drug delivery device (16), i.e. a needle, is introduced via the system (10) of the present invention. However, as described above, it is understood that the system (10) may be used to deliver a variety of medical instruments, such as imaging devices, catheter devices, surgical instruments and tools, energy sources, operative devices, implants, biopsy and specimen collection tools, and related medical diagnostic and treatment systems to any cellular locations within and adjacent to bodily cavities. In some advantageous embodiments, a diagnostic device, such as an ultrasound probe, is used with the system of the present invention. In additional advantageous embodiments, as shown in FIG. 11 an energy emitting device (68), such as a radiation emitting device, is delivered via the system (10).

As shown in FIG. 2A, the needle member (16) is movably disposed inside the outer shaft (12) adjacent the inner shaft (14) and the inflatable balloon (15) disposed at the distal end of the inner shaft. The needle (16) comprises an elongated shaft with at least one opening at a distal end thereof. The opening is fluidly connected with a needle lumen for delivering a desired therapeutic and/or diagnostic agent to tissue. The elongated shaft is made with any suitable biocompatible material, such as stainless steel or plastic, that is flexible enough such that the distal end of the needle (16) can be bent to a certain angle X once the balloon (15) is inflated, as illustrated in FIGS. 3B and 3C. In one advantageous embodiment, the elongated shaft with made with memory shape material, such as nitinol, such that the needle (16) will maintain its bent configuration.

Figures 8, 9:
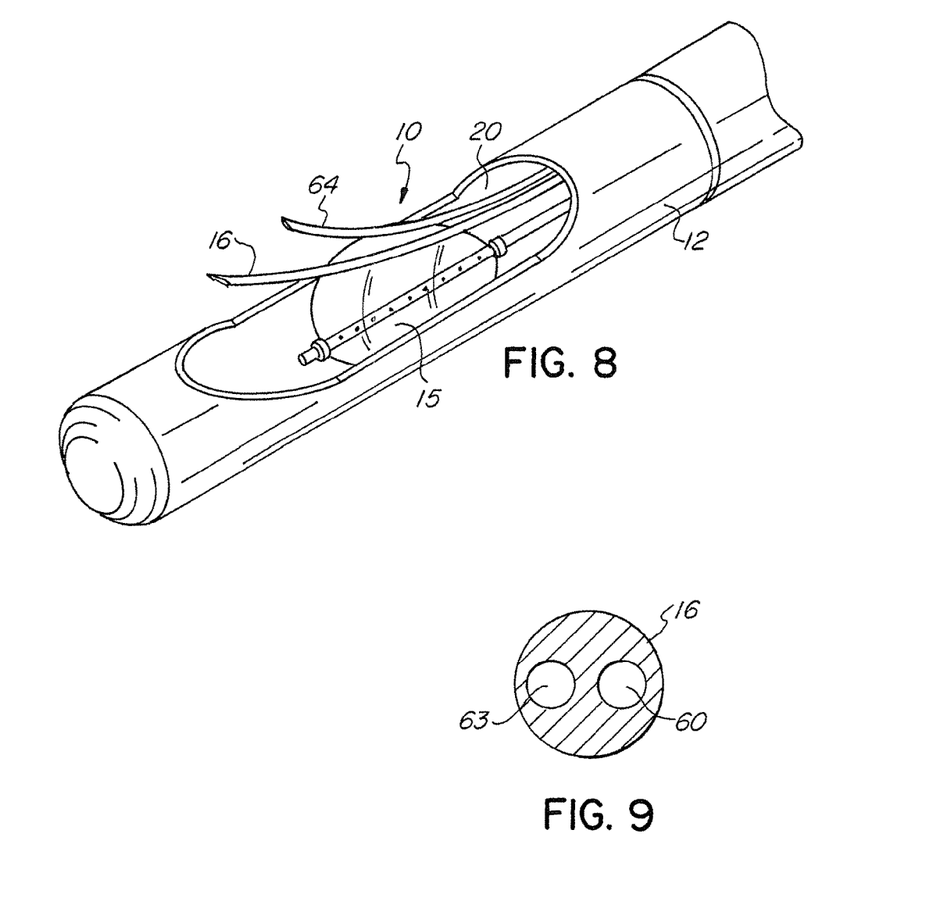
FIG. 8 is an enlarged perspective view of the distal end of the system of FIG. 1, showing two needles.
FIG. 9 is a cross-sectional schematic view of the needle member of the system of FIG. 1, having two lumens.

In some embodiments, the needle (16) has more than one inner lumen. For example, as shown in a cross-sectional view in FIG. 9, the needle (16) may have two delivery lumens (60, 63) for simultaneous or sequential delivery of two or more different therapeutic or diagnostic agents. It is understood that the needle member may have more than two lumens. In other embodiments, such as shown in FIG. 8, two needle members (16, 64) may be used to deliver two different agents. Once two needle members and/or one needle member with a dual inner lumen is inserted into a target tissue, different therapeutic and/or diagnostic agents are injected out of the distal tip of each needle and/or lumen opening, causing the agents to mix within the target tissue.

In one advantageous embodiment, the needle member (16) is used to deliver a polymerizing hydrogel to bodily tissue. One component of the hydrogel agent, such as hydrogel, is delivered through a first needle and/or needle lumen and a second component of the hydrogel agent, such as polymerization agent, is delivered through a second needle and/or needle lumen. Such delivery results in mixing of the two components at the distal tips of the two needles and/or two needle lumens inside the target tissue, which causes the hydrogel to polymerize inside the target tissue. Alternatively, the two components may be mixed outside or adjacent to target tissue. In addition, a plurality of needles and/or needle lumens can deliver a third agent, such as drug eluting microspheres or nanoparticles, into the polymerizing hydrogel.

Additionally, the needle (16) may have openings on its sides, which may be located at different lengths along the length of the needle, for delivering the therapeutic and/or diagnostic agents laterally and/or via the opening at the tip. While in some applications, the needle (16) punctures the targeted tissue, in other applications, the needle (16) does not enter the tissue, but instead, sprays the surface of the tissue with the drug.

In an advantageous embodiment, the needle member (16) further includes at least one sensor for measuring various characteristics of bodily tissue to facilitate precise and efficient delivery of the drug. For example, it may be desirable to measure oxygen concentration of tissue, such as cancerous tissue. Any type of suitable sensor can be used in accordance with the present invention. The sensors are positioned at or in proximity of the distal tip or any other suitable location along the needle.

In some advantageous embodiments, the needle member (16) may also include at least one conductive probe, e.g. an electrode or an optical device, such as an optical fiber, capable of conducting infra red (IR) light, near infra red (NIR) light, ultra violet (UV) light and/or ultrasound waves, to assist in diagnosis and/or treatment of specific medical conditions. In additional advantageous embodiments, an energy emitting device, such as a radiation emitting probe may be used in addition to, or in place of the needle member.

In further advantageous embodiments, needle member (16) can supply additional media to tissue, e.g. medical grade oxygen. For example, tumor tissues are known to be hypoxic (having low concentrations of oxygen), and do not respond well to radiation treatment. Therefore, measuring the oxygen pressure and delivering oxygen to increase the oxygen concentration, coupled with a synchronized triggering of the radiation treatment, is important in treatment of the tumor tissues. For example, partial pressure of oxygen in a target tumor tissue is measured first by a sensor provided on the needle member, then a biopsy tissue specimen is obtained via the needle member or other biopsy device. Next, an oxygenating agent is delivered to tumor tissue, if necessary together with a chemotherapeutic drug and/or any other therapeutic agent, via the needle member. Then, a radiation probe is inserted to locally deliver targeted radiation to the tumor tissue.

Additionally, the inner lumen of the needle member (16) may accommodate a medical instrument or device needed to perform a certain procedure. In some embodiments, the needle member (16) is capable of obtaining a tissue sample for biopsy via the opening in its distal end.

Figure 2B:
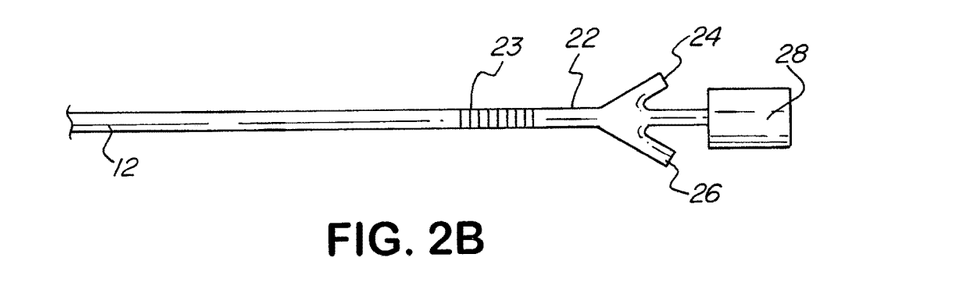
FIG. 2B is an enlarged schematic view of a proximal portion of the system of FIG. 1.
Figures 2C, 2D:
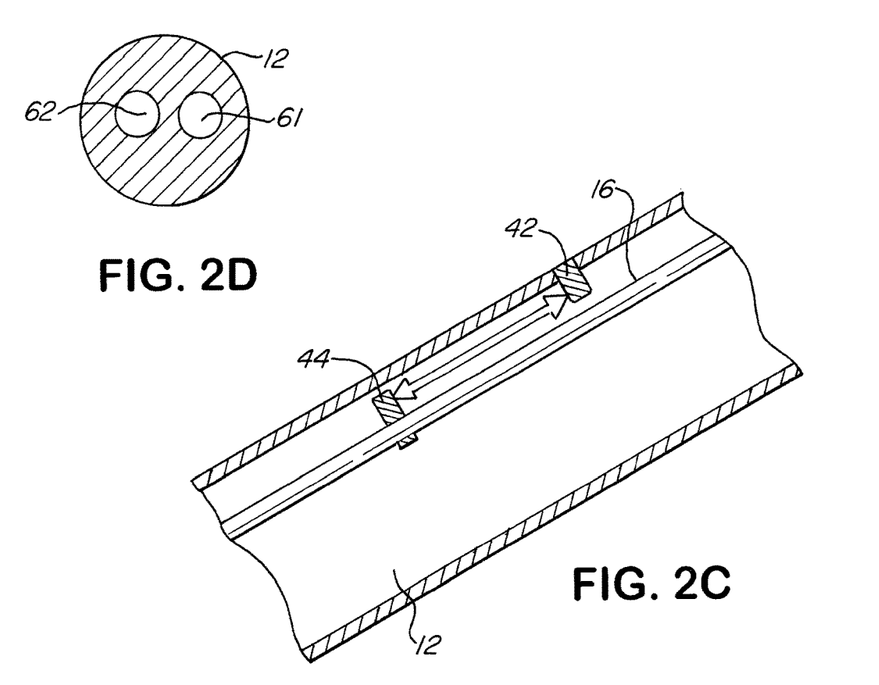
FIG. 2C is a cross-sectional schematic view of a proximal portion of the system of FIG. 1.
FIG. 2D is a cross-sectional schematic view of a distal portion of the system of FIG. 1.

In some advantageous embodiments, such as shown in FIG. 2D, the outer shaft (12) may have one or more inner lumens (61, 62) and/or partitioning walls for containing various components of the system (1), such as the inner shaft with the balloon, the needle member shaft, etc. The inner lumens (61, 62) assist in properly aligning and securing the balloon and the medical instrument/device being used such that the orientation of the medical instrument/device with respect to the balloon does not change as the balloon is inflated, for example, such that the needle will not slip with respect to the balloon. It is understood that more than two inner lumens may be provided in the outer shaft (12) for insertion of additional devices, such as, for example, an imaging device or a second inner shaft with a balloon, as discussed below. Furthermore, it is noted that the orientation of the inner lumens (61, 62) inside the outer shaft (12) shown in FIG. 2D is only exemplary, and that any other desired configuration of the inner shafts may be used in accordance with the present invention.

An imaging device and/or illumination device may also be employed with the system of the present invention. In some embodiments, a fiber optic image bundle (50) is introduced through the lumen of the outer shaft (12) center via a port provided at the proximal end to image the surrounding area. The fiber optic image bundle (50) can be made of an incoherent fiber bundle for illumination and a coherent imaging fiber bundle at the core, and a lens. The bundle (50) may incorporate various types of object lenses at the distal tip for different field of view (i.e. 50°, 130°, etc.) and various depth of field. Two separate bundles, one for illumination and the other for image can also be used. At the distal end (52) of the fiber optic bundle (50), the imaging coherent fibers are separated from illumination fibers and interfaced to an image sensor, such as CMOS or CCD, through appropriate optics. Similarly, the illumination fibers are interfaced to a light source. It should be noted, however, that other sources of illumination, such as light emitting diodes, may also be employed. It should also be noted that the image sensor can be located at the tip of the imaging catheter assembly, eliminating the need for coherent imaging fiber bundle, thus increasing the image quality and reducing cost.

The imaging and/or illumination device (50) provides the physician or user with illuminated light, non-thermal illuminated light, and direct visual feedback of the surrounding area. In some advantageous embodiments, the imaging/illumination device (50) is extended through the aperture (20) to illuminate and provide imaging of the target tissue site during the procedure and to facilitate positioning of the medical instrument, such as the needle (16). The distal end (52) of the imaging device (50) preferably has the ability to be actuated rotationally, thereby allowing for 360° visualization of the treatment area.

In further advantageous embodiments, the distal end (13) of the outer shaft (12) includes a transparent membrane made out of any suitable material. The imaging and/or illumination device (50) is extended through the outer shaft lumen to the membrane, which allows for visualization of the area ahead of the distal end (13) of the shaft (12). In this way, the physician can be provided with illuminated light and direct visual feedback of the area ahead of the system (10) during the insertion of the system into a patient's body.

In other advantageous embodiments, the lumen of the outer shaft (12), in which the imaging device (50) is disposed, has an opening at its distal end (13), and the imaging device (50) is extended out of the opening to visualize tissue in front of the system (10). The distal end of the imaging device (50) may include a lens cleaning device for cleaning the lens, such as described in U.S. patent application Ser. No. 13/480,153, the disclosure of which is also incorporated by reference herein in its entirety.

A proximal end of the system (10) is illustrated in FIG. 2B. The proximal end (22) includes an inflation port (24) for connection of the inner shaft (14) to the fluid source (18), through which the balloon (15) is inflated. The inflation port (24) is provided with any suitable connector, such as a luer connector, for connection to the fluid source (18). The proximal end (22) further includes a medical device insertion port (26), through which a desired medical instrument or device, such as a needle member, is inserted into the outer shaft (12). It is noted that additional ports may be provided at the proximal end (22) for insertion of additional devices. For example, a separate imaging port may be provided for insertion of the imaging device into the outer shaft (12). Alternatively, the imaging device may be inserted through the medical device insertion port (26).

In some advantageous embodiments, the proximal end (22) of the outer shaft (12) may include calibrated markings (23) to gauge extent of insertion of the outer shaft (12) into a bodily cavity.

The proximal end (22) may also be connected to a control device (28), such as a hand piece, for actuation of the system (10) by a physician. In some embodiments, the control device (28) is used to inflate and deflate the balloon (15) provided at the distal end of the inner shaft (14). In these embodiments, the fluid source (18) may be connected directly to the control device via any type of suitable connector. The control device (28) is also used to move the inner shaft (14) with the balloon (15) distally or proximally to facilitate more precise positioning of the balloon relative the medical instrument and the target tissue site. The inner shaft is actuated manually or pneumatically by supplying fluid and/or vacuum to any suitable pneumatic mechanism.

In additional advantageous embodiments, the control device (28) is also used to actuate the medical device, e.g. the needle member (16) disposed in the outer shaft (12) from its inactivated position, as shown in FIG. 3A, to its activated position shown in FIG. 3B, and vice versa. The medical device may be inserted directly into the control device (28) and may be actuated manually or via any suitable pneumatic mechanism. The medical device may also be rotated manually or via the control device to better position the device relative to the tissue site.

The control device (28) also enables rotational movement of the distal end of the outer shaft (12) and/or the distal end of the needle member (16). In some advantageous embodiments, the distal end of the outer shaft and/or the needle member may be rotated according to a defined ratio of torque applied at the proximal end of the outer shaft/needle member. In particularly advantageous embodiments, the torque ratio is 1:1 meaning that one turn at the proximal end causes a rotation of one turn at the distal end.

It should be noted that the actuation of various components of the system (10) may be controlled via any other suitable means, such as voice control or robotically, in accordance with the present invention.

The proximal end (22) of the system (10) further includes a stop feature to prevent the needle member (16) from advancing too far in the proximal direction of the outer shaft (12). In particular, when the needle member (16) is moved into its activated position illustrated in FIG. 3B, it is desirable to ensure that the sharp distal tip of the needle does not move past the inflatable balloon (15), such that it may puncture the balloon upon inflation. In order to achieve this, the proximal end of the outer shaft (12) includes a stop member (42), such as a stop ring, positioned on the inner surface of the outer shaft, as shown in FIG. 2C. The proximal end of the needle (16) includes a corresponding stop member (44) which interacts with the stop member (42) of the outer shaft to prevent the needle member from moving beyond a certain position.

It is understood that the stop feature illustrated in FIG. 2C is only exemplary and that any other suitable mechanism may be used in accordance with the present invention. It is also understood that the stop feature may be provided at any suitable location along the length of the outer shaft (12).

Figure 4A:
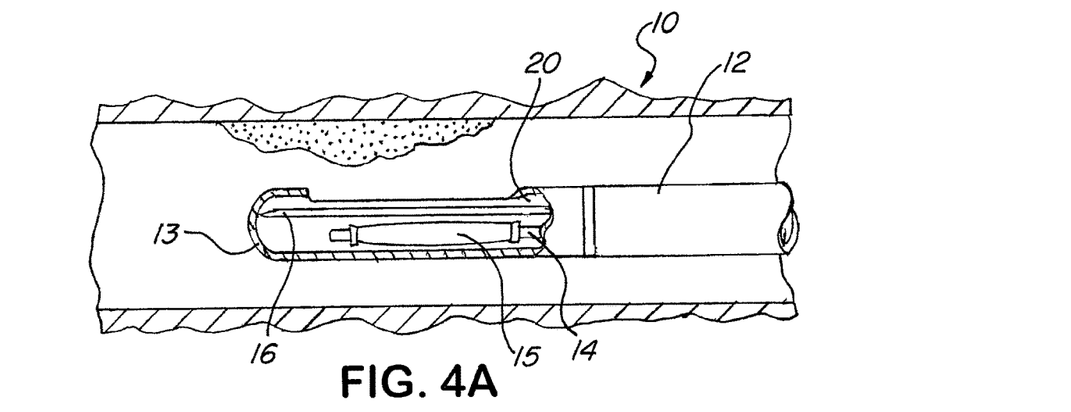
FIGS. 4A-4C are partially cross-sectional schematic views of the system of FIG. 1 being operated in a bodily cavity.
Figure 4B:
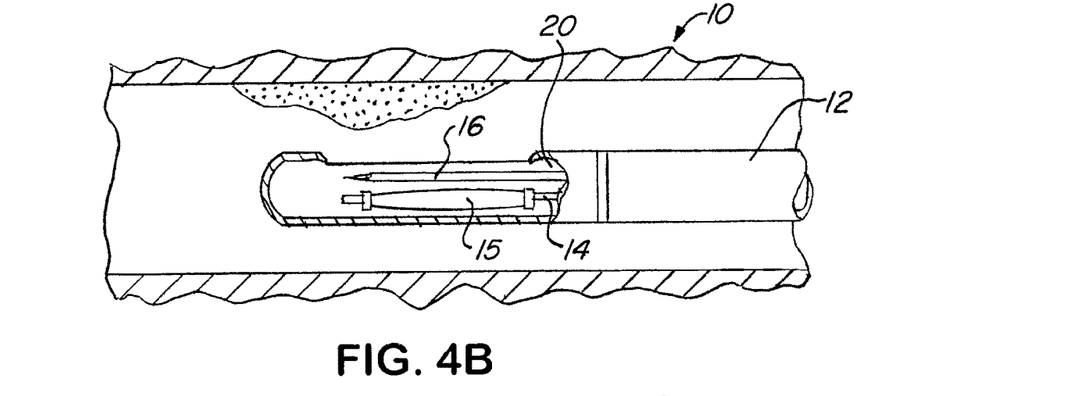
Figure 4C:
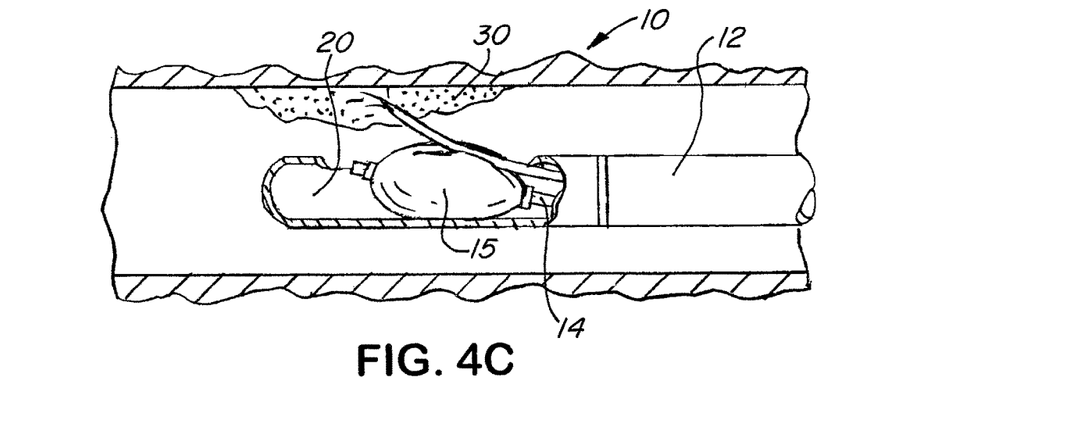

The method for delivering a medical instrument into a bodily cavity in accordance with the present invention is illustrated in FIGS. 4A-4C. As shown in FIG. 4A, in its inactivated position, the needle member (16) is extended to the distal tip (13) of the outer shaft (12) past the aperture (20). This way, the sharp tip of the needle member (16) remains completely housed by the outer shaft (12) thereby preventing possible injury to the patient during the insertion of the system (10) into the patient's body. The inner shaft (14) is also disposed inside the outer shaft (12) such that the balloon (15) in its deflated state is positioned adjacent the aperture (20).

Once the system (10) is inserted and positioned next to the target bodily cavity or tissue site (30), the needle member (16) is moved into an activated position), as illustrated in FIG. 4B. Specifically, the needle member (16) is moved a proximal direction until its distal tip is aligned with the aperture (20, such that the tip of the needle member (16) can be extended out of the aperture (20). The stop mechanism (42, 44) provided at the proximal end of the shaft (12) will prevent the needle member from advancing too far past the balloon, as described in more detail above.

Next, fluid is supplied to the inner shaft (14) from the fluid source to inflate the balloon (15). As the balloon (15) becomes inflated, it comes into contact with the distal end of the needle (16). Further inflation of the balloon (15) causes the needle (16) to deflect outwardly from the outer shaft such that it extends at a certain angle relative to a longitudinal axis of the outer shaft and come into contact with target tissue (30), as shown in FIG. 4C. The angle (X) at which the needle (16) extends outwardly from the outer shaft (12) will depend upon the particular medical procedure being performed, as well as the type of tissue and the desired depth of penetration. In an advantageous embodiment, the angle (X) at which the needle member (16) extends from the outer shaft is in the range of from about ten degrees to about sixty degrees.

The angle (X) is precisely controlled through the degree of inflation of the balloon (15), which in turn is controlled based on a number of predetermined or measured parameters. For example, the inflation of the balloon (15) may be based on the characteristics of a particular balloon, measurements of dimensions of a particular bodily cavity, and/or measurements of one or more vital signs and physiological parameters of the patient. The inflation of the balloon and the operation of the needle are also monitored by one of more imaging devices disposed in the outer shaft, as discussed above.

Once a desired angle (X) is reached, the needle member (16) may be moved further into tissue (30) to reach a desired penetration depth or to perform a necessary procedure, such as tissue sampling, tissue measurement, tissue resection, or the like. In the embodiment shown wherein the needle member is used, the therapeutic and/or diagnostic agent is supplied to tissue via the needle lumen. The balloon may be deflated and inflated repeatedly to adjust the positioning of the needle member (16) or to cyclically deliver the drug to tissue.

After the desired procedure is carried out completely, the balloon (15) is deflated, and the needle member (16) is moved distally into its inactivated position shown in FIG. 4A, wherein the distal tip of the needle is completely enclosed by the outer shaft (12). Then, the system is safely withdrawn from the patient's body.

Figure 5A:
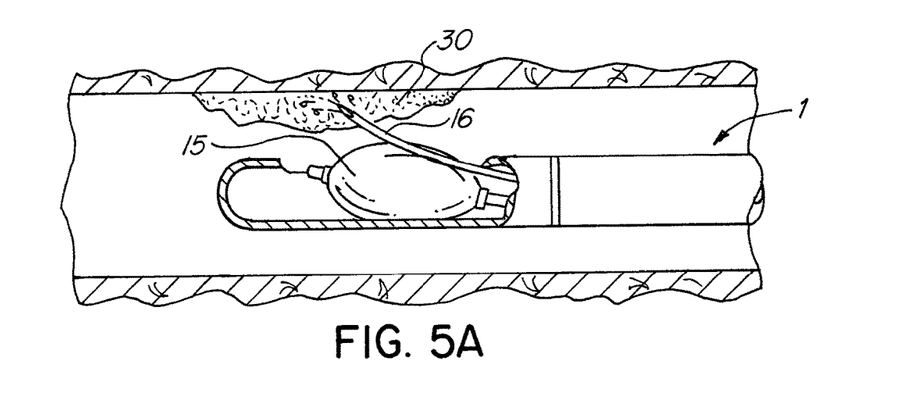
FIGS. 5A-5C are partially cross-sectional schematic views of the another embodiment of the system of FIG. 1 being operated in a bodily cavity.
Figure 5B:
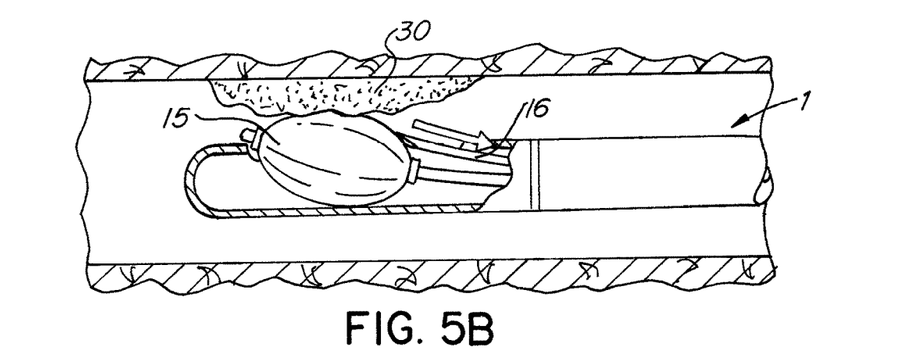
Figure 5C:
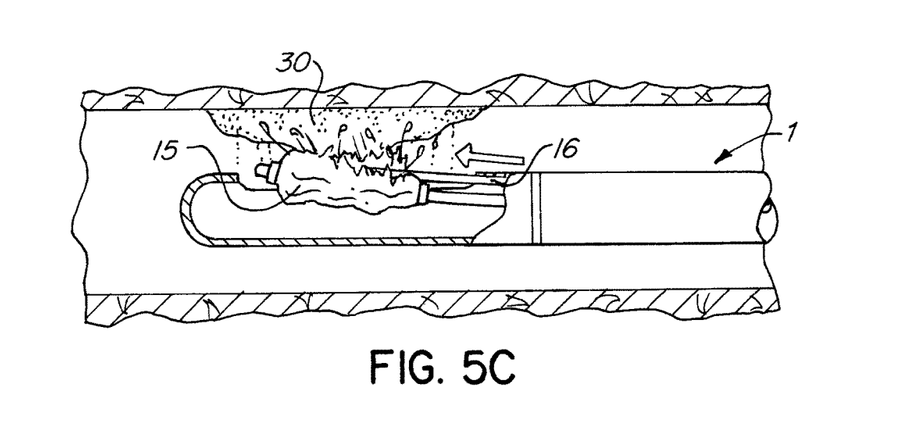

In some advantageous embodiments, such as shown in FIGS. 5A-5C, the needle member (16) may be used to intentionally puncture the balloon (15). For example, as shown in FIG. 5A, the system (1) is inserted into a patient's body and the balloon (15) is inflated to guide the needle member (16) toward the target tissue to inject a therapeutic/diagnostic agent into the tissue. After the desired agent is delivered to tissue via the needle member (16), the needle member is moved in a proximal direction, as shown in FIG. 5B, such that the distal tip of the needle member is placed adjacent the balloon wall. The needle member (16) is then moved toward the balloon (15), which causes the sharp distal end of the needle member (16) puncture the balloon wall, as illustrated in FIG. 5C. As a result the balloon is deflated and the system may be pulled out of the patient's body. In some embodiments, the balloon (15) contains a therapeutic/diagnostic agent, which is released once the balloon is punctured by the needle member.

Figure 6:
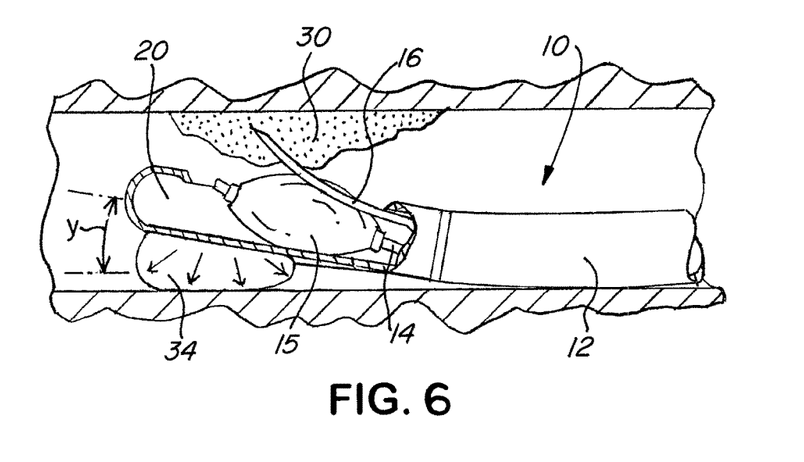
FIG. 6 is a partially cross-sectional schematic view of additional embodiment of the system of FIG. 1.

Another exemplary embodiment of the system of the present invention is shown in FIG. 6. In this embodiment, the system (10) further includes an expansion device (34) affixed to the side wall of the outer shaft (12) opposite of the aperture (20). As shown in 6, the expandable device (34) is an inflatable balloon having a half-sphere shape. A separate inflation lumen (not shown) may be provided in the outer shaft (12) to supply fluid from the fluid source (18) to the inflatable balloon (34). Once the system (10) is introduced into a patient's body and positioned adjacent the target tissue site, and the balloon (34) is inflated to cause the needle member (16) to extend out from the outer shaft (12) through the aperture (20), the balloon (34) is inflated such that it pushes against a bodily cavity wall. This will cause the distal end of the outer shaft (12), and in turn, the needle member (16) to come in closer contact with the tissue (30). This is particularly advantageous when the delivery probe is used in larger bodily lumens, wherein the outer shaft (12) is not large enough to reach the bodily cavity wall to deliver the therapeutic agent into it.

Figure 7:
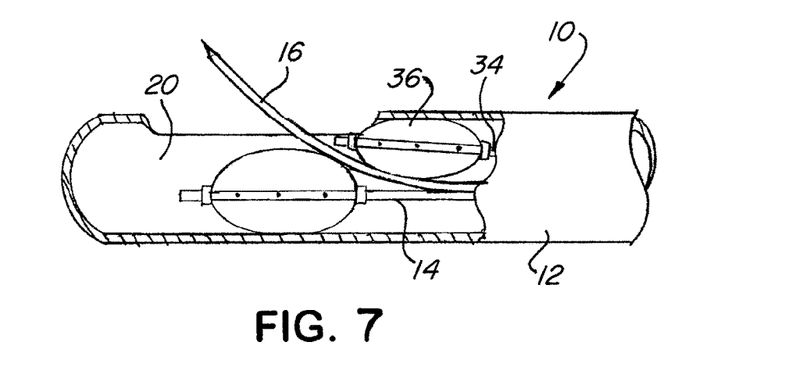
FIG. 7 is a partially cross-sectional schematic view of a further embodiment of the system of FIG. 1.

FIG. 7 illustrates a further advantageous embodiment of the system of the present invention. In this embodiment, the system (10) further includes a second inner shaft (34) disposed inside the outer shaft (12). The second inner shaft (34) has a second inflatable balloon (36) positioned at a distal end thereof, which is inflatable via a lumen provided in the second inner shaft (34) connected to the fluid source. Preferably, the second balloon (36) is inflatable separately from the first balloon (15). As shown in FIG. 7, the second balloon (36) is positioned proximally of the first balloon (15) such that the second balloon (36) is enclosed by the outer shaft (12) and does not extend out of the aperture (20) when inflated. The second balloon (36) is also oriented such that the needle member (16) or another medical instrument used is placed between the first balloon and second balloons when in the activated position. The first balloon (15) and the second balloon (36) are then inflated, either sequentially or simultaneously. The inflation of the first balloon (15) causes the needle to extend through the aperture away from the outer shaft (12), and the inflation of the second balloon (36) causes the needle (16) to deflect in an opposite direction toward the longitudinal axis of the outer shaft (12). This way, an angle at which the needle (16) is extended outwardly from the shaft can be controlled more precisely.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A system for delivering a medical instrument into a bodily cavity, comprising:
   an outer shaft having an aperture in a side wall thereof, wherein the aperture is provided at a distal portion of the outer shaft;
   an inner shaft positioned inside the outer shaft and having an inflatable balloon disposed at a distal portion thereof; and
   a needle member movably disposed in the outer shaft;
   wherein the balloon is in contact with and exerts a force on the needle member when the balloon is inflated such that the needle member extends outwardly from the outer shaft through said aperture; and
   wherein the balloon is movable longitudinally with respect to the needle member when the balloon is in an inflated state.

2. The system of claim 1, wherein the needle member extends outwardly from the outer shaft at an angle relative to a longitudinal axis of the outer shaft when in an activated position.

3. The system of claim 2, wherein the angle at which the needle member extends from the outer shaft is in the range of from about ten degrees to about sixty degrees.

4. The system of claim 1, wherein a distal end of the needle member extends past the aperture in the distal direction of the outer shaft when in an inactivated position.

5. The system of claim 1, further comprising a stop member provided on the needle member to prevent advancement of the needle member past the balloon in a proximal direction of the outer shaft.

6. The system of claim 1, further comprising an actuation member provided at a proximal end of the outer shaft for moving the needle member between an activated position and an inactivated position.

7. The system of claim 6, wherein the actuation member enables rotational movement of a distal end of the needle member.

8. The system of claim 1, further comprising a fluid source that supplies fluid to the balloon via a lumen of the inner shaft to inflate the balloon.

9. The system of claim 8, said fluid source comprises an electro-pneumatic pump.

10. The system of claim 8, wherein the fluid is a gas.

11. The system of claim 1, wherein the balloon has a wall with a textured outer surface.

12. The system of claim 11, wherein the textured surface of the balloon comprises a mesh disposed on the balloon wall.

13. The system of claim 12, wherein the mesh comprises elastane.

14. The system of claim 1, further comprising at least one imaging marker positioned at the distal end of the outer shaft adjacent said aperture.

15. The system of claim 1, wherein the outer shaft comprises an expansion apparatus affixed to the side wall of the outer shaft opposite said aperture.

16. The system of claim 1, wherein the needle member has at least one lumen fluidly connected to an opening at a distal end of the needle member.

17. The system of claim 16, wherein the needle member delivers a therapeutic and/or diagnostic agent to tissue via the opening at the distal end.

18. The system of claim 16, wherein the needle member obtains a tissue sample via the opening at the distal end.

19. The system of claim 16, wherein the at least one lumen of the needle member accommodates a medical instrument.

20. The system of claim 16, wherein the needle member has a first lumen fluidly connected to a first opening at the distal end of the needle member and a second lumen fluidly connected to a second opening at the distal end of the needle member.

21. The system of claim 1, further comprising a second needle member disposed in the outer shaft.

22. The system of claim 1, wherein the needle member comprises a memory-shape material.

23. The system of claim 1, further comprising an imaging device disposed in the outer shaft for viewing tissue in the bodily cavity.

24. The system of claim 23, wherein a distal end of the imaging device extends out through the aperture for viewing surrounding tissue.

25. The system of claim 23, wherein the imaging device is disposed in the inner shaft and extends out through an opening inside the inflatable balloon, and wherein an outer wall of the balloon is transparent for viewing surrounding tissue via the imaging device.

26. The system of claim 1, further comprising a second inner shaft positioned inside the outer shaft and having a second inflatable balloon disposed at the distal end thereof.

27. The system of claim 1, wherein the outer shaft comprises a first lumen for containing the inner shaft and a second lumen for containing the needle member.

28. A system for delivering a medical instrument into a bodily cavity, comprising:
an outer shaft having an aperture in a side wall thereof, wherein the aperture is provided at a distal portion of the outer shaft;
an inner shaft positioned inside the outer shaft and having an inflatable balloon disposed at a distal portion thereof; and
the medical instrument movably disposed in the outer shaft;
wherein the balloon is in contact with and exerts a force on the medical instrument when the balloon is inflated such that the medical instrument extends outwardly from the outer shaft through said aperture; and
wherein the balloon is movable longitudinally with respect to the medical instrument when the balloon is in an inflated state.

29. The system of claim 28, wherein the medical instrument is a biopsy instrument.

30. The system of claim 28, wherein the medical instrument is a drug delivery device.

31. The system of claim 28, wherein the medical instrument is a diagnostic device.

32. The system of claim 28, wherein the medical instrument is an energy emitting source.

33. A method for delivering a medical instrument into a bodily cavity, comprising the steps of:
inserting an outer shaft into a bodily cavity, said outer shaft having an inner shaft and a needle member disposed therein, and further having an aperture provided in a side wall thereof at a distal portion of the outer shaft; and
inflating a balloon disposed at a distal portion of said inner shaft such that the balloon contacts and exerts force on the needle member and causes it to extend outwardly from the outer shaft through said aperture;
wherein the balloon is movable longitudinally with respect to the needle member when the balloon is in an inflated state.

34. The method of claim 33, further comprising the step of extending the needle member past the aperture in the distal direction of the outer shaft before inserting the outer shaft into the bodily cavity.

35. The method of claim 33, further comprising the step of retracting the needle member in a proximal direction of the outer shaft after the outer shaft is inserted until the needle member is positioned adjacent the aperture.

36. The method of claim 35, wherein a stop member is provided on the needle member to prevent advancement of the needle member past the balloon in the proximal direction of the outer shaft.

37. The method of claim 33, wherein the needle member extends outwardly from the outer shaft at an angle relative to a longitudinal axis of the outer shaft when the balloon is inflated.

38. The method of claim 33, further comprising the step of puncturing balloon wall via the needle member.

\* \* \* \* \*